(12) United States Patent
Beylin et al.

(10) Patent No.: US 7,655,656 B2
(45) Date of Patent: Feb. 2, 2010

(54) HAIR GROWTH PROMOTING AGENTS

(75) Inventors: Vladimir Genukh Beylin, Ann Arbor, MI (US); Javier Magano, Ypsilanti, MI (US); Julie Kwon Spence, Ann Arbor, MI (US); James Anthony Wesley, Canton, MI (US)

(73) Assignee: Pfizer Inc., New York, NY (US)

( * ) Notice: Subject to any disclaimer, the term of this patent is extended or adjusted under 35 U.S.C. 154(b) by 417 days.

(21) Appl. No.: 11/572,032

(22) PCT Filed: Jul. 4, 2005

(86) PCT No.: PCT/IB2005/002150

§ 371 (c)(1),
(2), (4) Date: Jan. 12, 2007

(87) PCT Pub. No.: WO2006/008641

PCT Pub. Date: Jan. 26, 2006

(65) Prior Publication Data

US 2008/0318967 A1    Dec. 25, 2008

Related U.S. Application Data

(60) Provisional application No. 60/588,543, filed on Jul. 16, 2004.

(51) Int. Cl.
*C07D 405/12* (2006.01)
*A61K 31/501* (2006.01)
*A61P 17/14* (2006.01)

(52) U.S. Cl. .................. 514/252.01; 544/238
(58) Field of Classification Search ............ 514/252.01; 544/238
See application file for complete search history.

(56) References Cited

U.S. PATENT DOCUMENTS

| | | |
|---|---|---|
| 3,751,439 A | 8/1973 | Putney |
| 3,985,792 A | 10/1976 | Galat et al. |
| 5,912,244 A | 6/1999 | MacKenzie et al. |
| 2005/0182065 A1 | 8/2005 | Doherty et al. |

FOREIGN PATENT DOCUMENTS

WO    WO2004/043424 A    5/2004

OTHER PUBLICATIONS

Co-pending U.S. Appl. No. 10/699,895 corresponding to WO2004043424.
Co-pending U.S. Appl. No. 11/053,008 corresponding to WO2005079804.
Con-currently filed serial # not yet received claiming priority to U.S. Appl. No. 60/589,126 filed Jul. 19, 2004, corresponding to WO20061011046.

*Primary Examiner*—James O Wilson
*Assistant Examiner*—Cecilia M Jaisle
(74) *Attorney, Agent, or Firm*—Gregg C. Benson; J. Michael Dixon

(57) ABSTRACT

The present invention is directed to crystalline forms of 6-[[(3S,4R)-3,4-dihydro-3-hydroxy-6-[(3-hydroxypheny)sulfonyl]-2,2,3-trimethyl-2H-1-benzopyran-4-yl]oxy]-2-methyl-3(2H)-pyridazinone, formulations containing at least one of these crystalline forms and their use to promote hair growth.

8 Claims, 8 Drawing Sheets

HAIR GROWTH PROMOTING AGENTS

CROSS REFERENCE TO RELATED APPLICATION

This application is a Nationalization under 371 U.S.C. of International Application Number PCT/IB2005/002150 filed on Jul. 4, 2005 designating the United States, which claims the benefit of U.S. Provisional Application Ser. No. 60/588,543, filed on Jul. 16, 2004, the contents of each which are hereby incorporated by reference.

FIELD OF THE INVENTION

The present invention is directed to crystalline forms of the compound 6-[[(3S,4R)-3,4-dihydro-3-hydroxy-6-[(3-hydroxyphenyl)sulfonyl]-2,2,3-trimethyl-2H-1-benzopyran-4-yl]oxy]-2-methyl-3(2H)-pyridazinone.

BACKGROUND OF THE INVENTION

U.S. Pat. No. 5,912,244 ("the '244 patent") discloses the compound 6-[[(3S,4R)-3,4-dihydro-3-hydroxy-6-[(3-hydroxyphenyl)sulfonyl]-2,2,3-trimethyl-2H-1-benzopyran-4-yl]oxy]-2-methyl-3(2H)-pyridazinone (hereinafter "the Compound"), methods for its preparation and its use as a potassium channel opener. The '244 discloses that potassium channel openers may be used to treat diseases associated with altered tone or motility of smooth muscles. Examples of such conditions include chronic obstructive airway disease, asthma, urinary incontinence, hypertension, myocardial ischemia, cerebral ischemia, and glaucoma.

Example 7 of the '244 patent illustrates the preparation of the Compound, as the ethanol solvate. The ethanol solvate converts to an amorphous form over time. New crystalline forms of the Compound, having enhanced crystalline stability, would be an improvement over the prior art. Such forms would be more amenable to handling and formulating into finished dosage forms at clinical or industrial scale.

Copending, commonly assigned, U.S. patent application Ser. No. 60/544,116 (the '116 application) discloses the use of the Compound to promote hair growth in mammals. The '116 application discloses that the Compound stimulates the growth of the hair follicle, increases the number of follicles in the anagen phase and increases the period of time that follicles remain in the anagen phase (i.e., increases the anagen to telogen ratio).

SUMMARY OF THE INVENTION

In accordance with the present invention, new crystalline forms of 6-[[(3S,4R)-3,4-dihydro-3-hydroxy-6-[(3-hydroxyphenyl)sulfonyl]-2,2,3-trimethyl-2H-1-benzopyran-4-yl]oxy]-2-methyl-3(2H)-pyridazinone have been discovered. The structure of the Compound is depicted below:

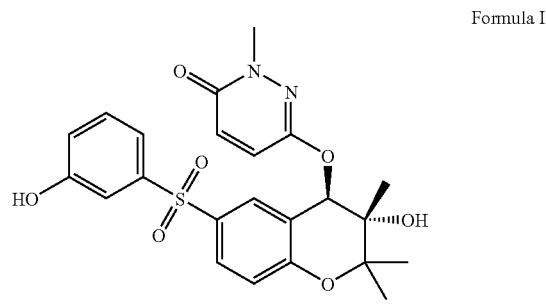

Formula I

One of the new crystalline forms is the dihydrate of 6-[[(3S,4R)-3,4-dihydro-3-hydroxy-6-[(3-hydroxyphenyl)sulfonyl]-2,2,3-trimethyl-2H-1-benzopyran-4-yl]oxy]-2-methyl-3(2H)-pyridazinone. The second new crystalline form is anhydrous (6-[[(3S,4R)-3,4-dihydro-3-hydroxy-6-[(3-hydroxyphenyl)sulfonyl]-2,2,3-trimethyl-2H-1-benzopyran-4-yl]oxy]-2-methyl-3(2H)-pyridazinone.

These new crystalline forms of the Compound are more amenable to handling and formulating in carriers for administration to mammals at clinical or industrial scale. The anhydrous crystalline form of the Compound is especially amenable to formulating and to industrial handling. Each of the crystalline forms can be distinguished by its powder X-ray diffraction (pXRD) pattern, or a combination of the pXRD pattern and its differential scanning calorimetry (DSC) thermogram.

Powder X-ray diffraction (pXRD) patterns were determined for the dihydrate and anhydrous crystalline forms of the Compound. The characteristic peaks are reported infra.

Either of the new crystalline forms of the Compound may be used as potassium channel openers. Either of the new crystalline forms of the Compound may be used to treat diseases associated with altered tone or motility of smooth muscles. In addition, either of the new crystalline forms of the Compound may be used to promote hair growth (including, but not limited to, treating or preventing alopecia). Alternatively, either of the new crystalline forms may be used in a dosage form for administration to a mammal. Alternatively, either of the new crystalline forms may be used for the manufacture of a topical dosage form, which may be applied directly to the area where promotion of hair growth is desired. In a more specific embodiment, the anhydrous crystalline form of the Compound may be used to promote hair growth. In another embodiment, the anhydrous crystalline form of the Compound may be used for the manufacture of a topical dosage form, which may be applied directly to the area of the skin where promotion of hair growth is desired In a further embodiment, the invention is directed to an article of manufacture containing a topical dosage form prepared from the anhydrous crystalline form of the Compound, packaged for retail distribution, in association with instructions advising the consumer how to use the product to promote hair growth.

DETAILED DESCRIPTION OF THE INVENTION

A) Definitions

Figure 1:
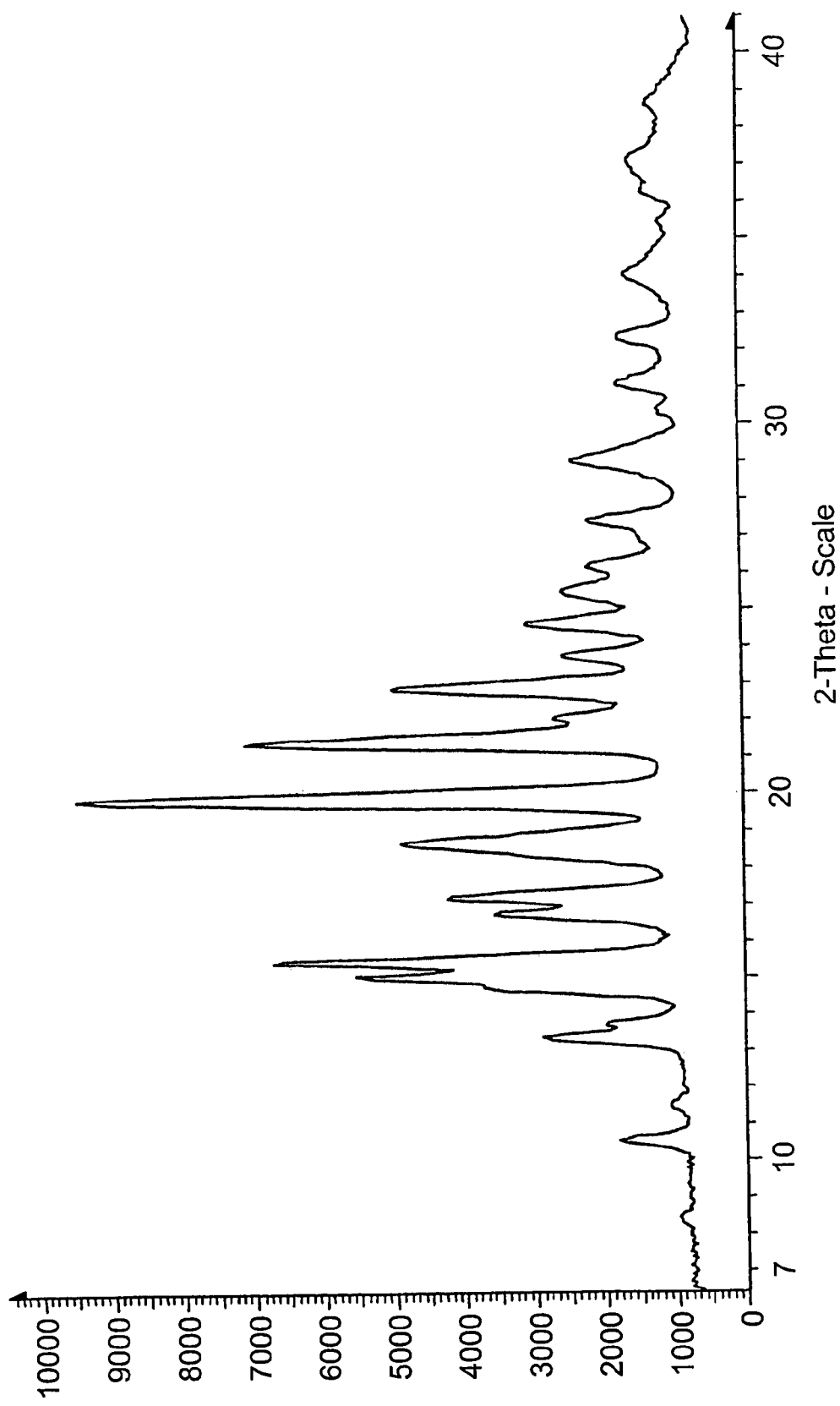
FIG. 1 depicts a powdered X-ray diffraction pattern of the anhydrous crystalline form of the Compound.

The disclosures of each patent, patent application and publication cited or described in this document are hereby incorporated herein by reference, in their entirety. Various modifications of the invention, in addition to those described herein, will be apparent to those skilled in the art from the foregoing description. Such modifications are also intended to fall within the scope of the appended claims.

As used throughout this application, including the claims, the following terms have the meanings defined below, unless specifically indicated otherwise. The plural and singular should be treated as interchangeable, other than the indication of number.
  a. The term "comprises" means includes, but is not limited to.
  b. "Mammal" includes humans, primates such as stump-tailed macaques, companion animals such as dogs, cats, gerbils, etc. and livestock such as cattle, swine, horses, llamas, and sheep.
  c. "admixture" means two or more components mixed together resulting in a combination of the components. By way of non limiting example, one component is dissolved in another component.
  d. "Promoting hair growth" includes stimulating an increase in total hair mass and/or length. Such increase includes increased length and/or growth rate of hair shafts (i.e. follicles), increased number of hairs, and/or increased hair thickness. Some or all of the above end results can be achieved by prolonging or activating anagen, the growth phase of the hair cycle, or by shortening or delaying the catagen and telogen phases. "Promoting hair growth" should also be considered to include preventing, arresting, decreasing, delaying and/or reversing hair loss.
  e. "Alopecia," as used herein, encompasses partial or full baldness, hair loss, and/or hair thinning.
  f. "Treating or alleviating alopecia" refers to promoting hair growth in mammals who have experienced, or are considered at risk for experiencing, alopecia.
  g. "Pharmaceutically acceptable" means suitable for use in mammals.
  h. "solvate" is a crystalline form of a compound or salt thereof, containing one or more molecules of a solvent of crystallization, i.e., the Compound or a salt thereof, containing solvent combined in the molecular form. An ethanol solvate of the Compound is a solvate in which the solvent is ethanol. A "hydrate" is a solvate in which the solvent is water.
  i. "Dermatologically acceptable" refers to a carrier which may be applied to the skin or hair, and which will allow the drug to diffuse to the site of action.
  j. "Compounds of the invention" and "Compounds", are being used interchangeably and should be treated as synonyms. Each refers to 6-[[(3S,4R)-3,4-dihydro-3-hydroxy-6-[(3-hydroxyphenyl)sulfonyl]-2,2,3-trimethyl-2H-1-benzopyran-4-yl]oxy]-2-methyl-3(2H)-pyridazinone. The Compound is also commonly referred to as (3S,4R)-[6-(3-hydroxyphenyl)sulfonyl]-2,2,3-trimethyl-4-(2-methyl-3-oxo-2,3-dihydropyridazin-6-yl-oxy)-3-chromanol, (3S,4R)-3,4-dihydro-4-(2,3-dihydro-2-methyl-3-oxopyridazin-6-yl)oxy-3-hydroxy-6-(3-hydroxyphenyl)sulphonyl-2,2,3-trimethyl-2H-benzo[b]pyran) (see Example 7 of U.S. Pat. No. 5,912,244. Other chemical names for the Compound represented by Formula I are also known and are included within the scope of the term "Compound" as used herein.

B) Methods of Characterization

A number of methodologies may be used in differentiating different crystalline forms of the same molecule. For instance, experimental x-ray powder diffraction (pXRD) patterns and differential scanning calorimetry (DSC) have been used to differentiate crystalline forms from one another. Each was used to characterize the anhydrous crystalline form of the Compound and the crystalline dihydrate of the Compound.

a. Experimental Powder X-ray Diffraction

Experimental powder x-ray diffraction (pXRD) is one means for determining whether a particular crystalline form of the Compound is the ethanol solvate, the dihydrate, the anhydrous crystalline form, or a new crystalline form. A discussion of the theory of X-ray powder diffraction may be found at Stout and Jensen, *X-ray Structure Determination; A practical guide,* MacMillan and Co. New York, N.Y. (1968). Further discussion of Experimental powder x-ray diffraction techniques may be found at Jenkins and Snyder, *Introduction to X-ray powder difractometry,* Wiley, New York, N.Y. (1996).

The experimental powder x-ray diffractions depicted in FIGS. I-III were carried out utilizing a Bruker D8 X-ray powder diffractometer with GADDS (General Area Diffraction Detector System) C2 system with a single Goebel mirror configuration. Scans were run with the detector at 15.0 cm. Theta 1, or the collimator, was at 7° and Theta 2, or the detector, was at 17°. The scan axis was 2-omega with a width of 3°. At the end of each scan Theta 1 is at 10° and Theta 2 is at 14°. Samples were run for 120 seconds at 40 kV and 40 mA with Cu radiation. Scans were integrated from 6.4° to 41° 2θ. Samples were run in ASC-6 sample holders purchased from Gem Dugout [State College, Pa.]. Sample was placed in the cavity in the middle of the sample holder, and flattened with a spatula to be even with the surface of the holder. All analyses were conducted at room temperature, which is generally 20° C. -30° C. Scans were evaluated using DiffracPlus software, release 2003, with Eva version 8.0.

As is readily apparent to one skilled in the art, the results of any X-ray powder diffraction pattern may vary. This variance can be due to sample preparation, the particular model of X-ray diffractometer used, the operator's technique, etc. Further, one skilled in the art will realize that the relative intensities of peaks present in an experimental pXRD pattern may vary due to the preferred orientation of a particular crystal and that the pXRD may be carried out using techniques to minimize these effects. Such techniques include, for example, grinding of the sample before analysis, spinning or rocking the sample during analysis, or utilization of a diffractometer equipped with an area detector. The term "approximately" if used in defining a position of a characteristic peak in an X-ray powder diffraction pattern is defined as the stated 2θ value ± 0.2° 2θ.

Figure 2:
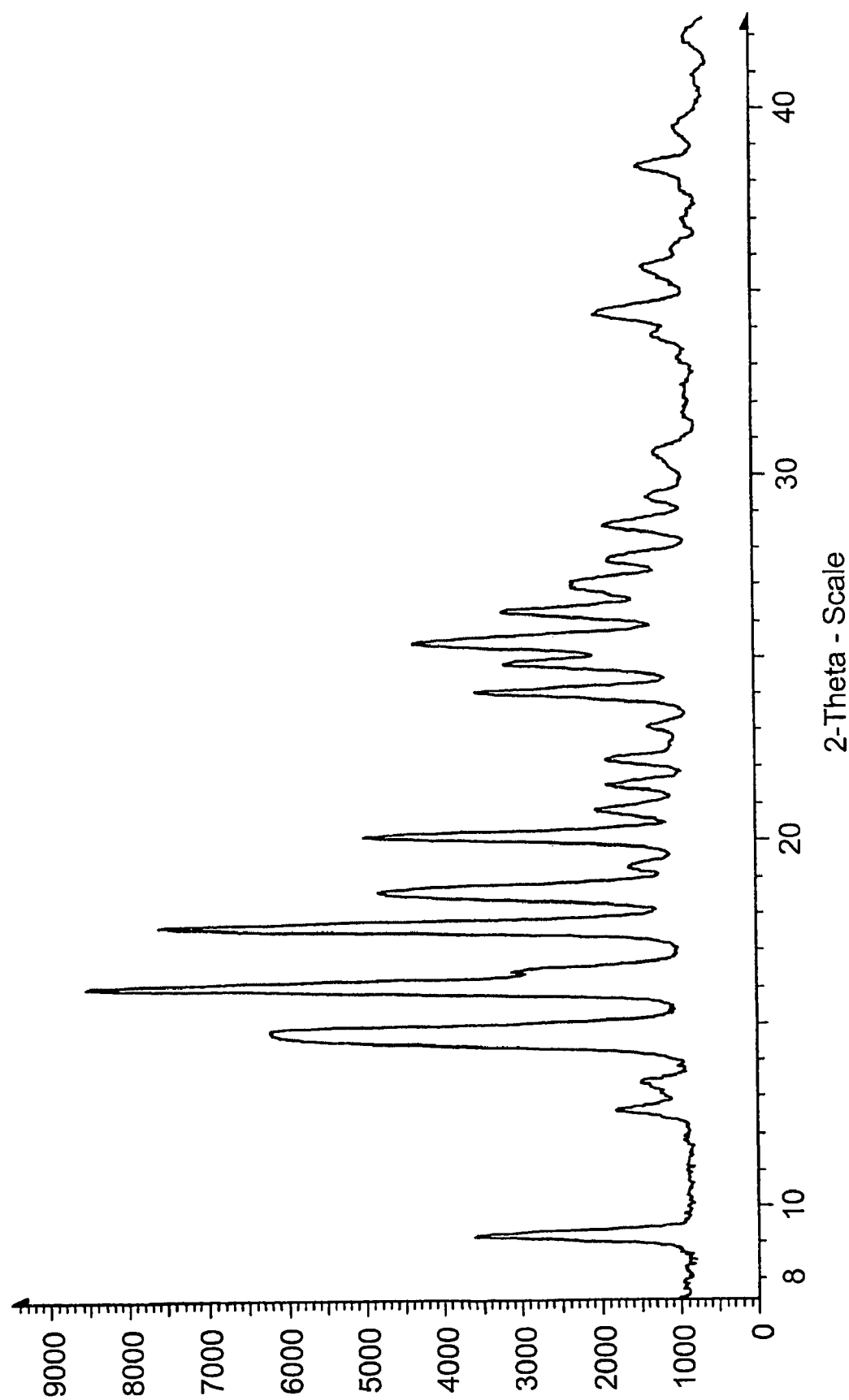
FIG. 2 depicts a powdered X-ray diffraction pattern of the dihydrate crystalline form of the Compound.

Thus, merely because an experimental pXRD is not identical to the pXRD's depicted in FIG. 1 or 2, does not mean that a crystalline form is not the dihydrate or anhydrous crystalline form of the Compound. As will be discussed infra, the presence of selected characteristic peaks, identified from the pXRD patterns, may be used to determine whether a crystalline form is the anhydrous crystalline form of the Compound, the crystalline ethanol solvate, the dihydrate crystalline form of the Compound, or a new form of the Compound.

b. Melting Point

All melting points described herein were determined by using DSC (differential scanning calorimetry). The ethanol solvate was run on a TA Instruments 2920 DSC (New Castle, Del.). The sample was weighed into a standard aluminum pan with a pinhole and crimped. Pans used were TA Instruments' part nos. 900786.901 (bottoms) and 900779.901 (tops). The sample was run using a ramp method of 3° C./minute to a temperature of 350° C., under nitrogen purge. One to five milligrams of sample were used. Further discussion of differential scanning calorimetry may be found at Clas, Dalton, and Hancock, *Differential scanning calorimetry: application in drug development*, Pharmaceutical Science and Technology Today, Volume 2, Number 8 (8 Aug. 1999).

The dihydrate crystalline form of the Compound and the anhydrate crystalline form of the Compound were run on a TA Instrument Q1000 series DSC. (New Castle, Del.). Both were also run in crimped aluminum pans with pinhole. These pans were weighed, and their weight was accounted for using TA instrument's Tzero Technology. Further discussion of Tzero Technology may be found at Cassel, *How Tzero Technology Improves DSC Performance. Part I: Flat Baselines and Glass Transition Measurements*, TA Instruments library Number TA272.

One to five milligrams of the dihydrate crystalline form of the Compound or the anhydrous crystalline form of the Compound was weighed. The method used for these samples was a modulated DSC or mDSC run. Further discussion of mDSC may be found at Coleman and Craig, *Modulated temperature differential scanning calorimetry: a novel approach to pharmaceutical analysis.* International Journal of Pharmaceutics 135 (1996) pages 13-29. For the dihydrate, the following parameters were used: Modulation Amplitude ± 2° C.; Modulation period-100 seconds; Underlying heating rate 3.0° C./min from 35° C. to 200° C. For the anhydrous crystalline form of the Compound, the following parameters were used: Modulation Amplitude ± 2° C.; Modulation period-60 sec; Underlying heating rate 1.5° C./minutes from 35° C. to 170° C.

c. Thermogravimetric Analysis (TGA)

Thermogravimetric analysis measures the change in mass of a substance as a function of time and temperature. Loss of mass in a TGA is due to solvent or water loss. Further discussion of TGA may be found at Rodiguez and Bugay, *Characterization of Pharmaceutical Solvates by Combined Thermogravimetric and Infrared Analysis.* Journal of Pharmaceutical Sciences, Volume 86, Number 2 (February 1997). The amount of water associated with the Compound was determined using TGA. All Thermogravimetric Analysis (TGA) were run on TA Instruments 2950 TGAs. (New Castle, Del.). Samples were run in standard Aluminum pans. Two to five mg of sample were used. Ramp rate was 10° C./minute to 400° C.

C) Anhydrous Crystalline Form of the Compound

One of the crystalline forms of the Compound is the anhydrous crystalline form. It has a melting point of 137° C. ± 3° C. The sample is anhydrous because no water is associated with the crystal lattice. However, the anhydrous form may adsorb surface water upon storage, depending on storage conditions with no subsequent conversion to the dihydrate.

The powder X-ray diffraction pattern of the anhydrous crystalline form of the Compound is depicted in FIG. 1. The pXRD pattern demonstrates several characteristic peaks associated with the anhydrous crystalline form of the Compound. A characteristic peak is one that has a significant relative intensity in the pXRD pattern and a 2θ position unique to the anhydrous crystalline form of Compound. The characteristic peaks of the anhydrous crystalline form of the Compound, expressed in degrees 2θ (approximate) are located at 10.5°, 15.0°, 17.2°, and 22.8°.

The presence of any one of the characteristic peaks at approximate 2θ values of 10.5°, 15.0°, 17.2°, and 22.8° in a crystalline sample of the Compound, submitted to experimental X-ray diffraction at a temperature of 20° C.-30° C., is sufficient to confirm that the sample is the anhydrous crystalline form. In a further embodiment, the presence of at least two or three of these peaks in a crystalline sample of the Compound, submitted to experimental X-ray diffraction, is sufficient to confirm that the sample is the anhydrous crystalline form. In a more specific embodiment, the presence of characteristic peak at approximate 2θ values 10.5°, 15.0°, 17.2° and 22.8° is sufficient to confirm that the crystalline substance is the anhydrous crystalline form of the Compound. Any experimental X-ray diffraction studies should be carried out as described above, to minimize the impact that preferred orientation may have on the pattern generated.

A review of FIG. 1 identifies that additional peaks may be present in any sample of the anhydrous crystalline form of the Compound. The most relevant peaks identified in the pXRD pattern, including the characteristic peaks identified above, is listed below in Table I. The data presented in Table I should be used to assist in the interpretation of an experimental X-ray diffraction pattern of a crystalline form of the Compound. The data should not be used to conclude that a crystalline sample of the anhydrous form of the Compound is not the anhydrous crystalline form due to the absence of one, or more, selected peaks.

TABLE I

| |
|---|
| 10.5*[1] |
| 13.3 |
| 14.7 |
| 15.0* |
| 15.4 |
| 16.7 |
| 17.2* |
| 18.6 |
| 19.8 |
| 21.4 |
| 22.8* |
| 24.6 |

*Characteristic peak
[1]All stated 2θ values are approximate

D). Dihydrate Form

The dihydrate crystalline form of the Compound is another crystalline form of the Compound identified to date. It has a melting point of 127° C. ± 3° C. The dihydrate can have anywhere between approximately 1.5 to 2.5 moles of water per mole of molecule associated with it.

The X-ray diffraction pattern of the dihydrate crystalline form of the Compound is depicted in FIG. 2. The pXRD pattern demonstrates several characteristic peaks associated with the dihydrate crystalline form of the Compound. A characteristic peak is one that has a significant relative intensity in the pXRD pattern and a 2θ position unique to the dihydrate crystalline form of Compound. The pXRD pattern demonstrates several characteristic peaks associated with the dihydrate crystalline form of the Compound, expressed in degrees 2θ (approximate), which are located at 9.2°, 20.1°, 24.0°, and 25.4° 2θ.

The presence of at least one of these characteristic peaks in a crystalline sample of the Compound, submitted to experimental X-ray diffraction at a temperature of 20° C.-30° C., is sufficient to confirm that the sample is the dihydrate form of the Compound. In a further embodiment, the presence of at least two, three, or four of these peaks in a crystalline sample of the dihydrate crystalline form of the Compound submitted to experimental X-ray diffraction is sufficient to confirm that the sample is the dihydrate crystalline form of the Compound. Any experimental X-ray diffraction should be carried out as described above, to minimize the impact that a preferred orientation may have on the pattern generated.

A review of FIG. 2 identifies that additional peaks may be present in any sample of the dihydrate crystalline form of the Compound. Relevant peaks identified in the experimental X-ray diffraction pattern carried out on a crystalline sample of the dihydrate of the Compound, including the characteristic peaks identified above, are listed below in Table II. The data presented in Table II should only be used to assist in the interpretation of an pXRD of a sample of the dihydrate crystalline form of the Compound. The data should not be used to conclude that a crystalline sample of the Compound is not the dihydrate crystalline form of the Compound due to the absence of one, or more, selected peaks.

TABLE II

| |
|---|
| 9.2*[1] |
| 14.8 |
| 16.0 |
| 16.4 |
| 17.6 |
| 18.6 |
| 20.1* |
| 20.8 |
| 24.0* |
| 24.8 |
| 25.4* |
| 26.2 |
| 27.0 |

*Characteristic peak
[1]All stated 2θ values are approximate

E) Ethanol Solvate

Figure 3:
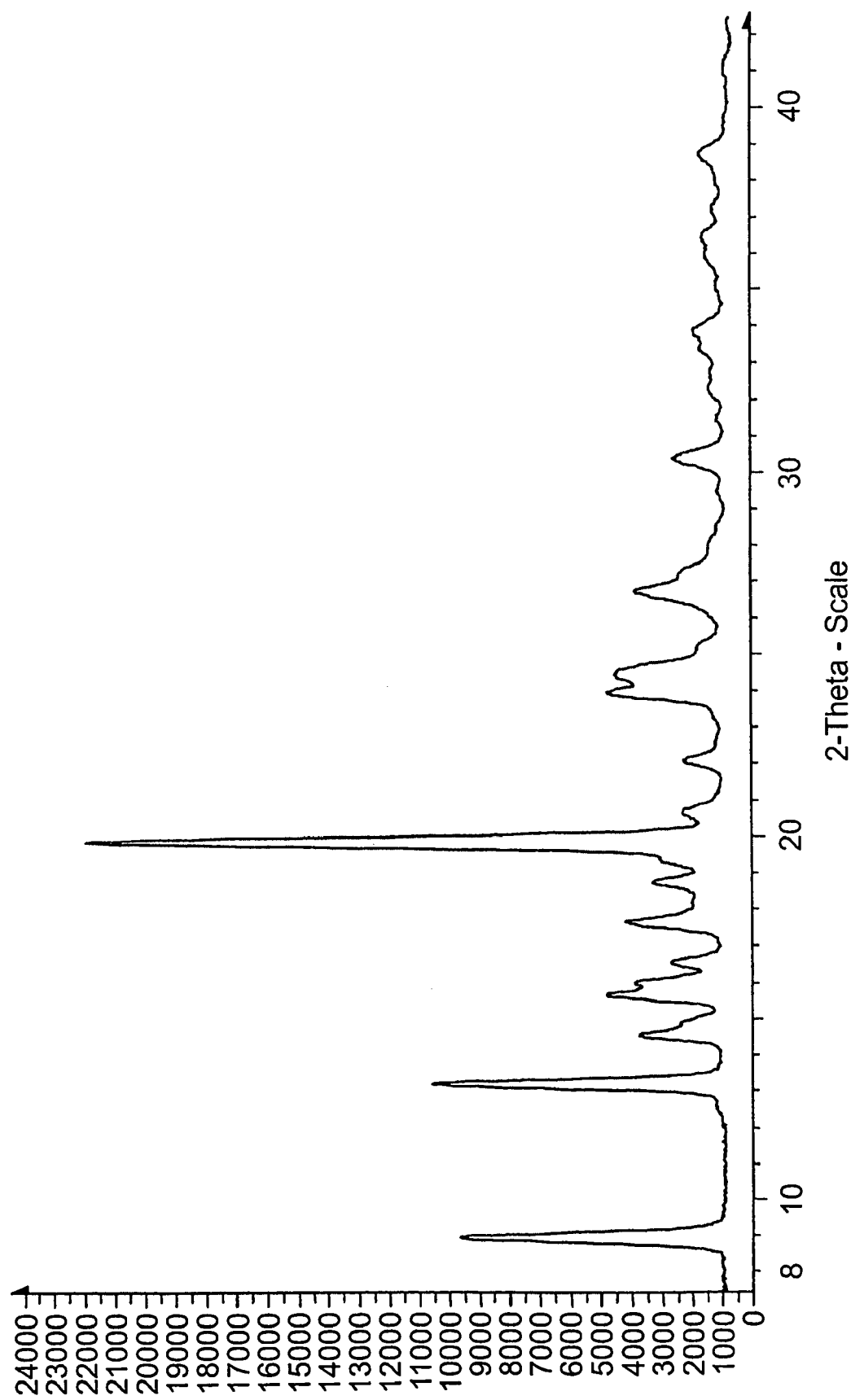
FIG. 3 demonstrates a powdered X-ray diffraction pattern of the ethanol solvate of the Compound.
Figure 4:
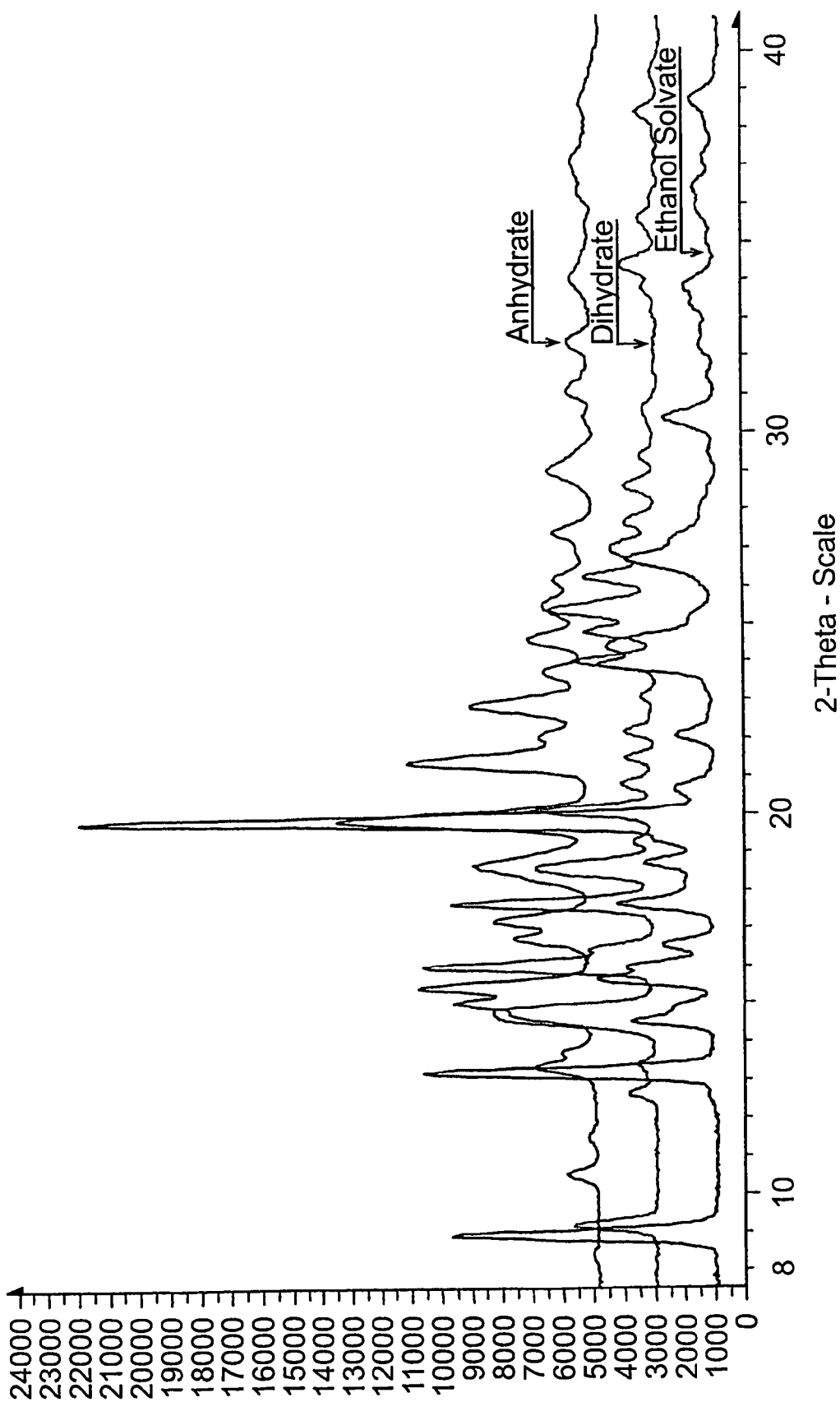
FIG. 4 demonstrates a comparison of powdered X-ray diffraction patterns of the anhydrous crystalline form, the dihydrate crystalline form and the ethanol solvate of the Compound.
Figure 5:
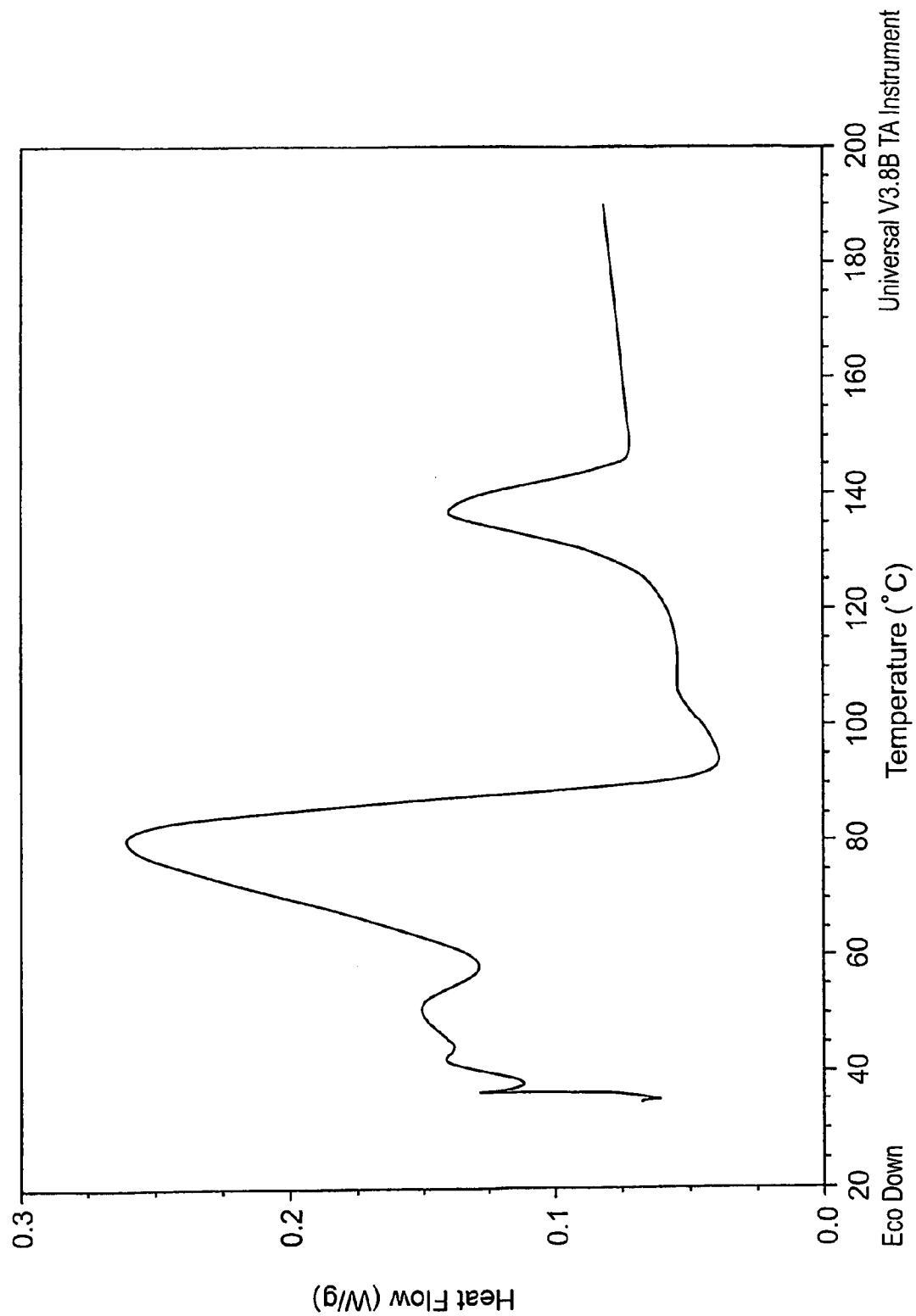
FIG. 5 represents a DSC of the dihydrate crystalline form of the Compound.
Figure 6:
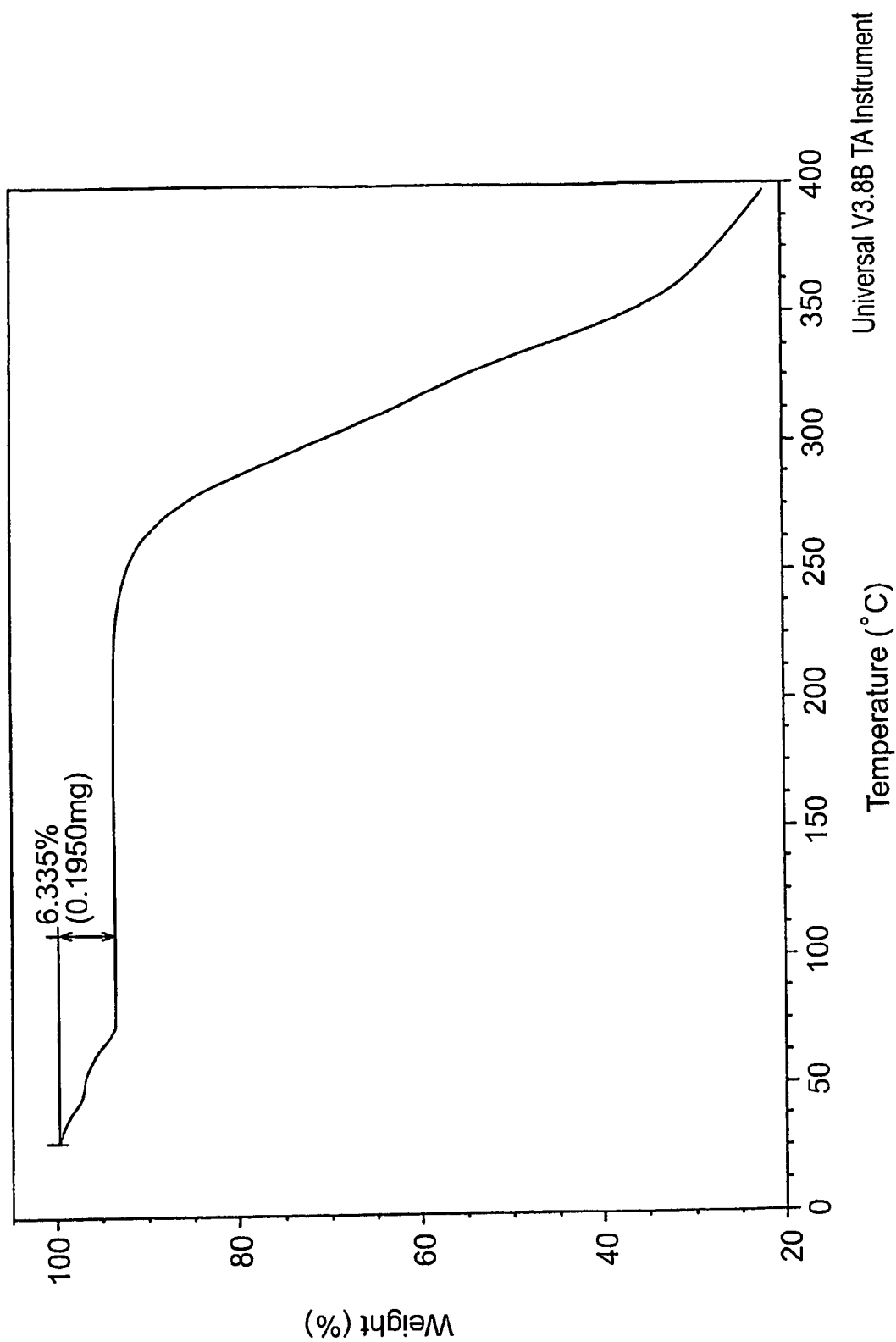
FIG. 6 represents a thermogravimetric analysis (TGA) of the dihydrate crystalline form of the Compound.
Figure 7:
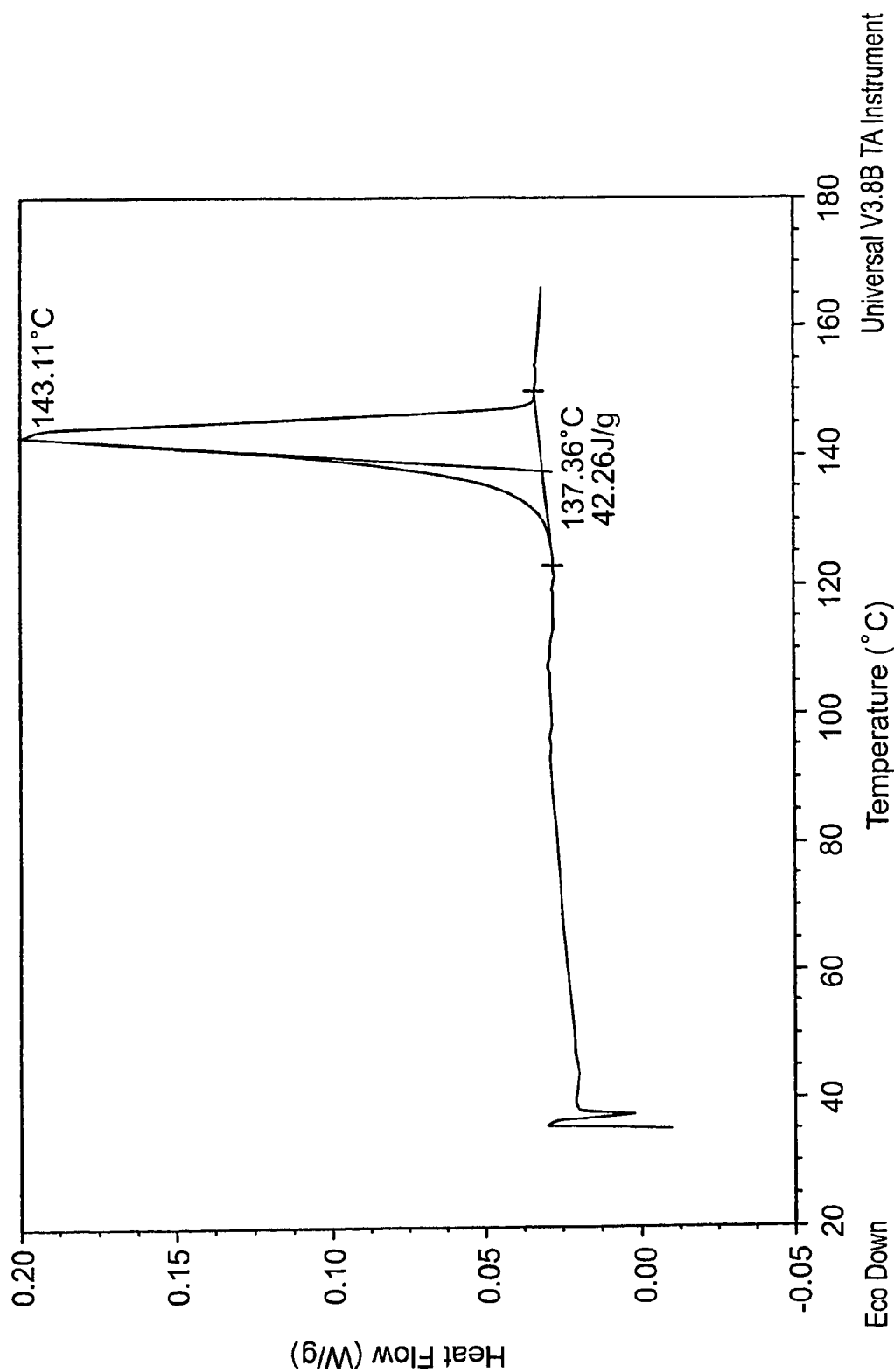
FIG. 7 represents a DSC of the anhydrous crystalline form of the Compound.
Figure 8:
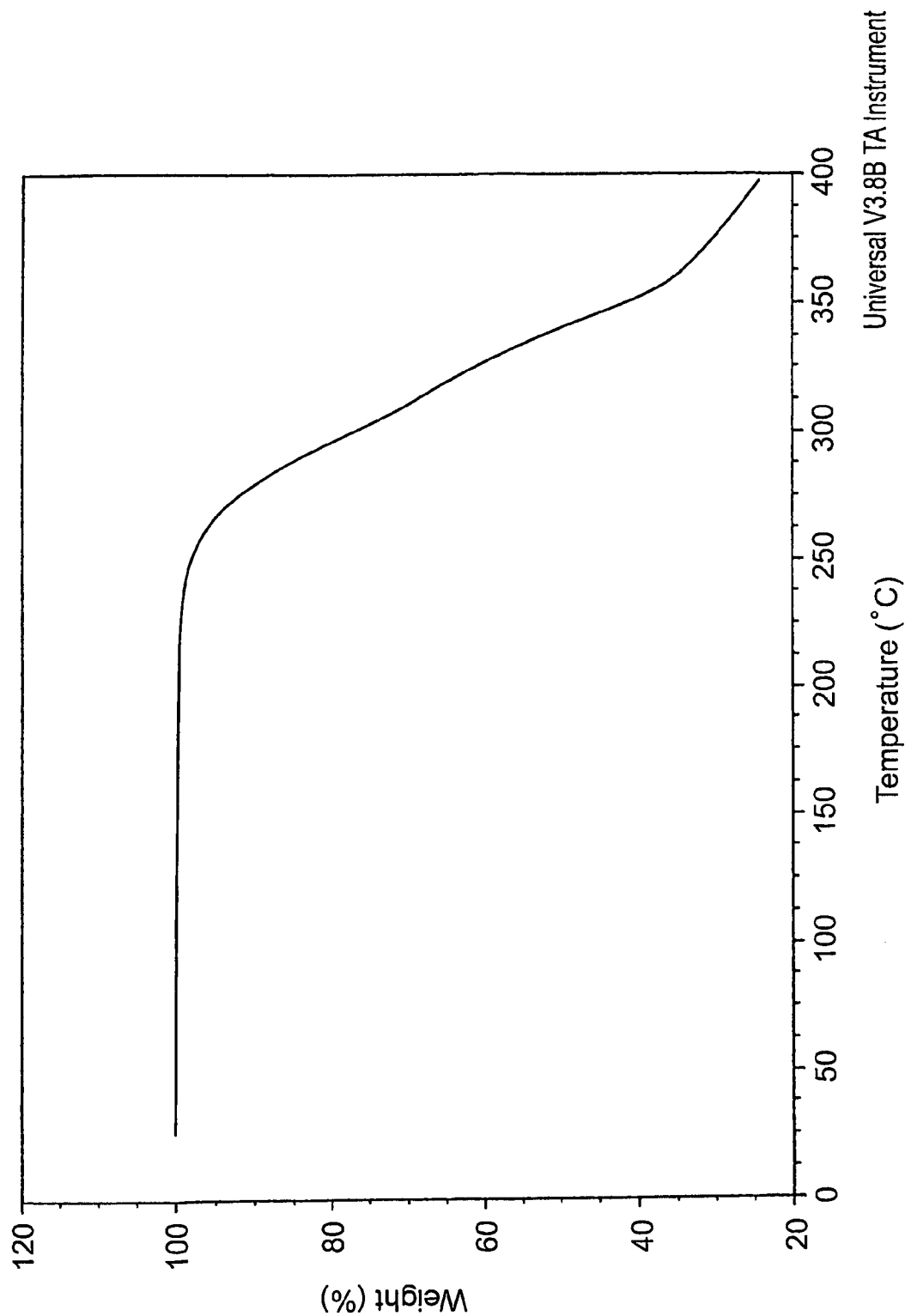
FIG. 8 represents a TGA of the anhydrous crystalline form of the Compound.

The X-ray diffraction pattern of the ethanol solvate form of the Compound is depicted in FIG. 3.

F) Method Of Preparation

The anhydrous crystalline form of the Compound and the dihydrate crystalline form of the Compound may be prepared using techniques generally known in the art. The initial step is to prepare the Compound, which may accomplished following the synthesis described in Example 7 of the '244 patent, which is hereby incorporated by reference.

The dihydrate crystalline form of the compound is prepared by contacting the ethanol solvate with water and heating the admixture at elevated temperatures for an extended period of time (typically about 50° C. for up to 4 days). The crystalline dihydrate may be recovered by filtration as is known in the art. Example 2 describes such a reaction in further detail.

The anhydrous crystalline form of the Compound is prepared by dehydrating the dihydrate. For example, the crystalline dihydrate is contacted with heat under a partial vacuum. Example 3 describes such a reaction.

G) Pharmacology And Dose

As noted above, the '244 patent and the '116 patent application describe the pharmacology of the Compound. It is a potassium channel opener. It may be used to promote the growth of hair in a mammal. The anhydrous crystalline and dihydrate crystalline forms of the Compound are also potassium channel openers (the "crystalline forms of the Compound"). They may be used in the same manner described in the '116 patent application to prolong the anagen to telogen ratio. Thus, the crystalline forms of the Compound may be used to promote hair growth.

The crystalline forms of the Compound may also be used in the preparation of topical dosage forms to promote hair growth, as desired by the user, or to prevent a decrease in hair growth in a subject.

In a typical embodiment, the crystalline forms of the Compound are used to manufacture formulations containing the Compound. Typically, the formulation will be suitable for topical administration to a mammal. More typically, it will be used to promote hair growth. Such formulations will generally be applied directly to the scalp, especially to those areas in which hair is absent, or thinning. The dose will vary, but as a general guideline, the Compound will be present in a dermatological formulation comprising a dermatologically acceptable carrier in an amount of from 0.01 to 10 w/w %, and the dermatological formulation will be applied to the area to be treated from 1 to 4 times daily. More typically, the Compound will be present in a quantity of from 1 to 3 w/w %, and the Compound will be applied once or twice daily.

In a further embodiment, the formulations can also be used to treat patients who have not yet experienced hair loss, but believe that they are at risk of doing so. Examples of such patients include those who will be undergoing cancer chemotherapy with a drug regimen known to induce alopecia. Young adults experiencing mental distress at the thought of balding, especially those with a family history of baldness, may also benefit from such prophylactic treatment. Such prophylactic treatment is encompassed by the term "promoting hair growth".

Hair growth results from a dynamic cyclic process of hair follicles and many common disorders of hair growth relate to alterations in the timing of the hair growth cycle. The hair growth cycle includes a growth phase (anagen), a transition phase (catagen) and a resting phase (telogen). During healthy hair growth situations, over 90% of scalp hair follicles are in anagen, 7% to 9% are in telogen and 1% to 3% are in catagen.

Anagen is the growth phase, during which the follicle (i.e. the hair root) penetrates deep into the dermis with the cells of the follicle dividing rapidly and differentiating. During the differentiation process, the hair cells synthesize keratin, the predominant component of hair. In non-balding humans, this growth phase lasts from one to five years.

Catagen is the transitional phase and is marked by the cessation of mitosis. Catagen generally lasts from about two to three weeks.

Telogen is the resting phase in which the hair is retained within the scalp for up to 12 weeks, until it is displaced by new follicular growth from the scalp below.

In humans, this growth cycle is not synchronized. An individual will have thousands of follicles in each of these three phases. However, most of the hair follicles will be in the anagen phase. In healthy young adults, the anagen to telogen ratio can be as high as 9 to 1. In individuals with alopecia, this ratio is reduced to as low as 2:1.

The most common form of hair loss is androgenic alopecia, a hereditary decrease of cosmetically useful hair induced by androgens in genetically predisposed men and women. This condition is also commonly referred to as male pattern baldness and female pattern baldness. While androgens are associated with some forms of balding, the physiological mechanism by which this hair loss occurs is not known. However, it is known that hair growth is altered in individuals afflicted with alopecia. The crystalline forms of the Compound may be used to manufacture a product to promote hair growth in individuals suffering from this type of alopecia. Hair loss also occurs in a variety of in other conditions.

Anagen effluvium, is hair loss due to chemicals or radiation, such as chemotherapy or radiation treatment for cancer. It is also commonly referred to as "drug induced" or "radiation induced" alopecia. The crystalline forms of the Compound may used be to manufacture preparations to treat these types of alopecia.

Alopecia areata is an autoimmune disorder which initially presents with hair loss in a rounded patch on the scalp. It can progress to the loss of all scalp hair, which is known as alopecia totalis and to the loss of all scalp and body hair, which is known as alopecia universalis. The crystalline forms of the Compound may be used to manufacture preparations to treat these types of alopecia.

Traumatic alopecia is the result of injury to the hair follicle. It is also commonly referred to as "scarring alopecia". Psychogenic alopecia occurs due to acute emotional stress. By inducing anagen, the Compound can be beneficial in these types of alopecia as well. Thus, the invention should not be construed as being limited to treating androgenetic alopecia. The crystalline forms of the Compound can be used to manufacture preparations to alleviate any type of hair loss.

The crystalline forms of the Compound may be used to manufacture preparations to promote hair growth in other mammals besides humans. For example, the Compound may be used with farm animals such as sheep, in which fur (hair) growth would exhibit an economic benefit. The Compound may also be used to stimulate hair growth in companion animals such as dogs, cats, gerbils, etc. The dosages required to obtain this effect will fit within the guidelines described above. Likewise, the Compound may be administered using formulations typically used for veterinary applications, taking into account the type of animal being treated. Other applications of the crystalline forms of the Compound to promote hair growth will become readily apparent to one skilled in the art based upon the disclosure of this application and should be considered to be encompassed by the claims.

As a general guideline, the preparations manufactured from crystalline forms of the Compound will be administered topically. They will be applied directly to the areas of the skin requiring hair growth promotion.

H) Pharmaceutical Formulations

If desired, the crystalline forms of the Compound can be administered directly without any carrier.

However, to ease administration, it will typically be formulated with at least one pharmaceutically acceptable or cosmetically acceptable carrier (herein collectively described as a "carrier"). Likewise, they will most typically be formulated into dermatological, or cosmetic carriers. In this application, the terms "dermatological carrier" and "cosmetic carrier" are being used interchangeably. They refer to formulations designed for administration directly to the skin or hair. The term "carrier," as used herein, means one or more compatible solid or liquid fillers, diluents, vehicles or encapsulating substances, which are suitable for administration to a mammal. The term "compatible," as used herein, means that the components of the composition are capable of being commingled with a compound as described herein, and with each other, in a manner such that there is no interaction that would substantially reduce the efficacy of the composition under ordinary use situations. Carriers must, of course, be of sufficiently high purity and sufficiently low toxicity to render them suitable for administration to the mammal (preferably the human being) being treated. The carrier itself can be inert or it can possess pharmaceutical and/or cosmetic benefits of its own.

The crystalline forms of the Compound may be formulated in any of a variety of suitable forms, for example, oral, topical or parenteral administration. Standard pharmaceutical formulation techniques may be used, such as those disclosed in *Remington's Pharmaceutical Sciences*, Mack Publishing Company, Easton, Pa. (1990).

Depending upon the particular route of administration, a variety of carriers well known in the art may be used. These include solid or liquid fillers, diluents, hydrotropes, surface-active agents and encapsulating substances. Optional pharmaceutically active or cosmetically active materials may be included which do not substantially interfere with the activity of the compound used in the methods of the present invention. The amount of carrier employed in conjunction with the compound used in the methods of the present invention is sufficient to provide a practical quantity of material for administration per unit dose of the compound. Techniques and compositions for making dosage forms useful in the methods of the present invention are described in the following references: *Modern Pharmaceutics,* Chapters 9 and 10, Banker & Rhodes, eds. (1979); Lieberman et al., *Pharmaceutical Dosage Forms: Tablets* (1981); and Ansel, *Introduction to Pharmaceutical Dosage Forms*, 2nd Ed., (1976).

Typically, the crystalline forms of the Compound are administered topically. The carrier of the topical composition may aid penetration of the compound into the skin to reach the environment of the hair follicle. Such topical compositions may be in any form including, for example, solutions, oils, creams, ointments, gels, lotions, pastes, shampoos, leave-on and rinse-out hair conditioners, milks, cleansers, moisturizers, sprays, aerosols, skin patches and the like.

A variety of carrier materials well known in the art for topical application, such as, for example, water, alcohols, aloe vera gel, allantoin, glycerine, vitamin A and E oils, mineral oil, propylene glycol, and the like can be used to prepare such formulations. The references discussed above disclose a number of excipients that can be used to prepare such topical dosage forms.

The Compound may also be administered topically in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. A potential formulation for topical delivery of the compound used in the methods of the present invention utilizes liposomes such as described in Dowton et al., "Influence of Liposomal Composition on Topical Delivery of Encapsulated Cyclosporin A: I. An in vitro Study Using Hairless Mouse Skin", S.T.P. Pharma Sciences, Vol. 3, pp. 404-407 (1993); Wallach and Philippot, "New Type of Lipid Vesicle: Novasome®", Liposome Technology, Vol. 1, pp. 141-156 (1993); U.S. Pat. No. 4,911,928; and U.S. Pat. No. 5,834,014.

Carriers for systemic administration include, for example, sugars, starches, cellulose and its derivatives, malt, gelatin, talc, calcium sulfate, vegetable oils, synthetic oils, polyols, alginic acid, phosphate buffer solutions, emulsifiers, isotonic saline and pyrogen-free water. Suitable carriers for parenteral administration include, for example, propylene glycol, ethyl oleate, pyrrolidone, ethanol and sesame oil.

Various oral dosage forms can be used, including such solid forms as tablets, capsules, granules and bulk powders. These oral forms comprise an effective amount, usually at least about 5% of the compound. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

Orally administered compositions also include liquid solutions, emulsions, suspensions, powders, granules, elixirs, tinctures, syrups and the like. The carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, Avicel RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents or colorants as described above.

Other compositions useful for attaining systemic delivery of the compound useful in the methods of the present invention include sublingual, buccal and nasal dosage forms. Such compositions typically comprise one or more soluble filler substances such as sucrose, sorbitol and mannitol; and binders such as acacia, microcrystalline cellulose, carboxymethyl cellulose and hydroxypropyl methylcellulose. Glidants, lubricants, sweeteners, colorants, antioxidants and flavoring agents described above may also be included.

Topical formulations are often prepared in the form of emulsions. The term "emulsion", as used herein refers to mixtures of two or more liquids, which may be in the form of a continuous phase and a disperse phase, for example. Exemplary emulsions may be in the form of creams, lotions, ointments, gels, etc. and may include, for example, oil-in-water emulsions, water-in-oil emulsions, multiple emulsions and microemulsions. These formulations will be prepared which contain from about 0.001 to 10 w/w % of the Compound. These formulations will then be applied to the desired areas from 1 to 4 times daily. Alternatively, these formulations will be applied to the desired areas less frequently, i.e., from 1 to 5 times a week.

Typically, the crystalline forms of the Compound will be incorporated into carriers suitable for topical administration. Any of the topical formulations described above or known in the art may be used. Examples of such topical formulations include lotions, sprays, creams, ointments, salves, gels, etc. Actual methods for preparing topical formulations are known or apparent to those skilled in the art, and are described in detail in Remington's Pharmaceutical Sciences, 1990 (supra); and Pharmaceutical Dosage Forms and Drug Delivery Systems, 6th ed., Williams & Wilkins (1995).

The formulations prepared from the crystalline forms of the Compound may also be used in combination with sunscreens (UVA or UVB blockers) to protect against sun or UV-induced damage.

In a further embodiment, the formulations described above may be packaged for retail distribution (i.e., a kit or article of manufacture). The package will contain instructions advising the patient how to use the product in order to promote hair growth. Such instructions may be printed on the box, may be a separate leaflet or printed on the side of the container holding the formulation, etc.

I) Examples

The following examples are presented in order to further illustrate the invention. They should not be construed as limiting the invention in any manner.

Example 1

Preparation of the Ethanol Solvate of the Compound

This Example illustrates one alternative method for the preparation of the ethanol solvate of (3S,4R)-[6-(3-hydroxyphenyl)sulfonyl]-2,2,3-trimethyl4-(2-methyl-3-oxo-2,3-dihydropyridazin-6-yl-oxy)-3-chromanol.

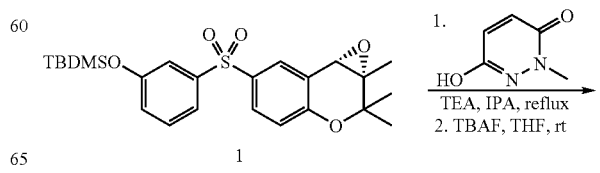

-continued

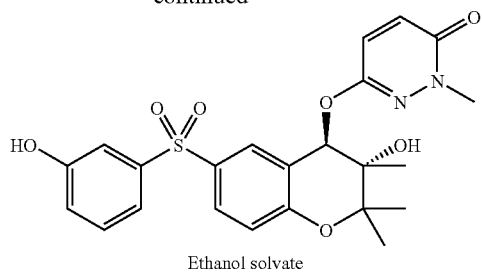

Ethanol solvate

Compound 1 (92.97 g, 202 mmol), 1-methyl-3,6-(1H,2H)-pyridazinedione (76.4 g, 605 mmol) and triethylamine (TEA) (85 ml, 605 mmol) were dissolved in isopropyl alcohol (IPA) (550 ml) in a one-necked, 2-L round bottomed-flask and the mixture was refluxed for 28 h and, then, cooled down to 20° C.

In order to remove the remaining TBDMS-protecting group, 200 ml of a 1M tetrabutylammonium fluoride (TBAF) solution in THF was added and the mixture was stirred for 30 minutes at room temperature. This completed the removal of the TBDMS protecting group and the solvent was stripped under vacuum to give a very dark brown oil which was dissolved in ethyl acetate (2 L) and the resulting mixture was washed with water (1×1.5 L, 3×500 ml), removing the aqueous phase after each wash step. After the final water wash, the organic phase was washed with saturated, aqueous NaCl solution (500 ml). The organic layer was transferred to an erlenmeyer flask and dried over MgSO$_4$ (50 g) at room temperature for 15 minutes. The solvent was removed under vacuum to give 95.9 g of a dark brown solid, which was purified by chromatography (3 kg of silica gel; mobile phase: ACN (acetonitrile), ACN/MeOH (99:1,v/v), ACN/MeOH (98.5:1.5 v/v) to give 57.6 g of a beige solid. The beige solid was dissolved in the solvent CH$_2$Cl$_2$ (200 ml) and filtered through a plug of celite (20 g) placed on a coarse, sintered-glass filter to remove any insoluble particles. The solvent was removed under vacuum and the resulting solid was dissolved in 95% ethanol, filtered through a coarse, sintered-glass filter to remove some insoluble material and concentrated under vacuum in a rotary evaporator at 17 torr to a final volume of about 200 ml. The solution was seeded with some crystals of the ethanol solvate and the flask was placed in a freezer at −5° C. for 20 h. The solid thus obtained was filtered through a course, 600-ml, sintered-glass filter, washed twice with 20 ml of cold ethanol (5° C.); and pressed dry on the filter to give 25.87 g of the Compound as an off-white solid. The mother liquors were concentrated to a very small volume (about 75 ml), seeded with some crystals of the ethanol solvate and the flask was placed in the same freezer for 20 hours to give, after following the same isolation procedure as above, 7.61 g of the Compound as an off-white solid.

Example 2

Preparation of the dihydrate crystalline form of the Compound

The ethanol solvate prepared in Example 1 (320.27 g) was slurried with vigorous stirring in 6.4 L of water (20 ml of water per gram of ethanol solvate) at 50° C. Some foamy material remained on top of the aqueous layer. After 2 days, a sample was drawn with a pipette, filtered immediately while still warm and dried for 1 hour (h) in a vacuum oven at 22° C. and 17 torr. pXRD analysis of the sample, performed as described above, showed complete conversion to the dihydrate form. TGA analysis of the sample, performed as described above, showed a value close to the theoretical 2 moles of water per mol of parent compound. In order to ensure complete conversion to the dihydrate, the mixture was stirred for 4 more days under the same conditions. The heating was stopped and the flask was placed in a water bath with some ice chips and its contents allowed to reach 20° C. The suspension was filtered, the solid pressed dry on the filter and, then, placed in a vacuum oven at 22° C. for 24 hours to remove the superficial water without affecting the dihydrate composition. TGA analysis showed about 2 moles of water per mol of parent compound.

Example 3

Preparation of the anhydrous, crystalline form of the Compound

The anhydrous crystalline form of the Compound was prepared from the ethanol solvate, slurrying the ethanol solvate to the dihydrate, and then dehydrating the dihydrate to form the anhydrous crystalline form.

One-gram of the dihydrate was placed on a Petri dish and dried in an oven at atmospheric pressure under a nitrogen blanket. The temperature was slowly increased from 18° C. to 120° C. at 0.1° C./minute. The drying at 120° C. was monitored by pXRD and mDSC.

The first sample was taken after 40 hours and was crystalline anhydrous material as determined by pXRD and mDSC. The estimated crystallinity was at 92% to 96%.

Drying was continued with samples taken after 64 hours and 88 hours. No significant change was noted. The material was cooled to 25° C. at 1° C./min. The final test showed 94% to 96% crystallinity.

Example 4

Preparation of an anhydrous, crystalline form of the Compound

The anhydrous crystalline form of the Compound may be prepared by ramping the temperature up to between about 40° C. to about 130° C. A ramp rate of from about 0.1° C./minute to about 10° C./minute may be used. The sample may be dried under pressures ranging from atmospheric pressure to a vacuum of about 3 torr.

An anhydrous crystalline form of the Compound was prepared from the white solid prepared in Example 2 by drying it on a tray at 60° C. under high vacuum (3 torr) for 21 h. The tray was weighed and put back in the oven for another 26 hours. No change in weight was observed. 285.33 g of the Compound was obtained as a white, powdery solid. The crystallinity of the white, powdery solid was determined by mDSC to be approximately 60% anhydrous crystalline form and about 40% amorphous form of the Compound.

What is claimed is:

1. Anhydrous crystalline 6-[[(3S,4R)-3,4-dihydro-3-hydroxy-6-[(3-hydroxyphenyl)sulfonyl]-2,2,3-trimethyl-2H-1-benzopyran-4-yl]oxy]-2-methyl-3(2H)-pyridazinone that exhibits an experimental powder x-ray diffraction pattern having at least one characteristic peak at approximate 2θ values selected from the group consisting of 10.5°, 15.0°, 17.2° and 22.8°.

2. The crystalline form of claim 1 that exhibits an experimental powder X-ray diffraction pattern, having characteristic peaks at approximate 2θ values of 10.5° and 17.2°.

3. The crystalline form of claim 1 that exhibits an experimental powder X-ray diffraction pattern, having characteristic peaks at approximate 2θ values of 10.5° and 22.8°.

4. The crystalline form of claim 1 that exhibits an experimental powder X-ray diffraction pattern having characteristic peaks at approximate 2θ values of 10.5°, 17.2° and 22.8°.

5. A pharmaceutical formulation for promoting hair growth prepared from an effective amount of a crystalline form according to claim 1 in admixture with at least one pharmaceutically acceptable carrier.

6. A method of preparing an anhydrous crystalline compound according to claim 1 comprising dehydrating the dihydrate form of the compound at a ramp rate of from about 0.1° C./minute to about 10° C./minute to a temperature ranging from about 40° C. to a temperature of about 120° C., and holding the resulting compound at the ending temperature for up to 48 hours.

7. The method of claim 6 comprising dehydrating the dihydrate form of the compound at a ramp rate of about 0.1° C./minute from about 18° C. to about 120° C., under atmospheric pressure, and holding the resulting compound about 48 hours under about atmospheric pressure.

8. The method of claim 6 comprising dehydrating the dihydrate form of the compound by heating the dihydrate form under a vacuum of 3 torr to about 60° C., and holding the resulting compound for up to about 48 hours under 3 torr vacuum.

* * * * *

UNITED STATES PATENT AND TRADEMARK OFFICE
CERTIFICATE OF CORRECTION

PATENT NO. : 7,655,656 B2  Page 1 of 1
APPLICATION NO. : 11/572032
DATED : February 2, 2010
INVENTOR(S) : Beylin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 438 days.

Signed and Sealed this

Twenty-third Day of November, 2010

David J. Kappos
*Director of the United States Patent and Trademark Office*